United States Patent [19]

Weeks

[11] Patent Number: 4,530,792
[45] Date of Patent: Jul. 23, 1985

[54] PROCESS AND INTERMEDIATES FOR PREPARATION OF 1,1-DIOXOPENICILLANOYLOXYMETHYL 6-BETA-AMINOPENICILLANATE

[75] Inventor: Paul D. Weeks, Gales Ferry, Conn.
[73] Assignee: Pfizer Inc., New York, N.Y.
[21] Appl. No.: 438,228
[22] Filed: Nov. 1, 1982
[51] Int. Cl.$^3$ ............... C07D 499/42; A61K 31/425
[52] U.S. Cl. ........................ 260/245.2 R; 260/239.1
[58] Field of Search ............. 260/245.2 R; 424/270, 424/271

[56] References Cited

U.S. PATENT DOCUMENTS

| | | | |
|---|---|---|---|
| 3,896,110 | 7/1975 | Sellstedt | 260/239.1 |
| 4,234,579 | 11/1980 | Barth | 424/246 |
| 4,244,951 | 1/1981 | Bigham | 424/250 |
| 4,342,772 | 8/1982 | Godtfredsen et al. | 424/271 |
| 4,359,472 | 11/1982 | Hamanaka | 260/245.2 R |
| 4,364,957 | 12/1982 | Barth | 260/245.2 R |
| 4,376,076 | 3/1983 | Kellogg | 260/245.2 R |

OTHER PUBLICATIONS

B. Baltzer et al., Journal of Antibiotics, 33, 1183 (1980).

*Primary Examiner*—Nicholas S. Rizzo
*Attorney, Agent, or Firm*—Charles J. Knuth; Albert E. Frost; Paul D. Thomas

[57] ABSTRACT

A process for the preparation of 1,1-dioxopenicillanoyloxymethyl 6-beta-aminopenicillanate which comprises reacting 1,1-dioxopenicillanoyloxymethyl 6-phenylacetamidopenicillanate or the corresponding phenoxyacetamidopenicillanate under anhydrous conditions with a halogenating agent in the presence of a reaction inert solvent to form an intermediate imino halide, addition of a primary alcohol having from one to four carbon atoms to convert the imino halide to an imino ether and subsequent hydrolysis to give the desired product.

10 Claims, No Drawings

PROCESS AND INTERMEDIATES FOR PREPARATION OF 1,1-DIOXOPENICILLANOYLOXYMETHYL 6-BETA-AMINOPENICILLANATE

BACKGROUND OF THE INVENTION

1. Field of the Invention

The invention relates to a process for preparation of 1,1-dioxopenicillanoyloxymethyl 6-beta-aminopenicillanate by deacylation of a compound of the formula

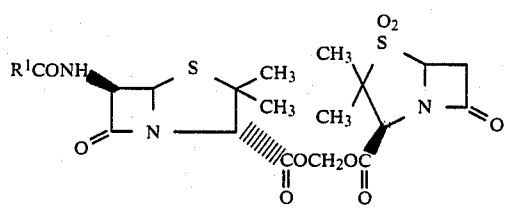

and to intermediate imino chlorides and imino ($C_1$–$C_4$)-alkyl ethers.

2. Description of the Prior Art

Penicillanic acid 1,1-dioxide (sulbactam) is known from U.S. Pat. No. 4,234,579 to be an effective beta-lactamase inhibitor and antibacterial agent.

U.S. Pat. No. 4,244,951 and U.S. Pat. No. 4,342,772 disclose bis esters of the formula

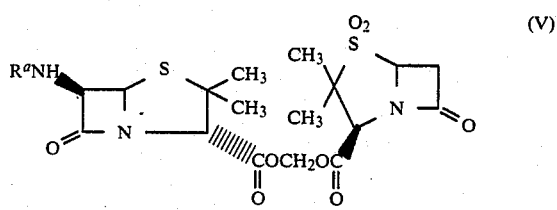

wherein $R^a$ is H or certain acyl groups of known antibacterial agents. For example, $R^a$ can represent 2-phenylacetyl, 2-phenoxyacetyl, D-2-amino-2-phenylacetyl or D-2-amino-2-(p-hydroxyphenyl)acetyl. Also disclosed are methods for preparing the above compounds wherein $R^a$ is said acyl by acylation of the 6-amino compound of formula (V) where $R^a$ is hydrogen. The latter compound is prepared by coupling the appropriate derivatives of penicillanic acid 1,1-dioxide and 6-protected-aminopenicillanic acid and removal of protecting group from the coupled product of formula (V) where $R^a$ is an amino-protecting group, e.g. benzyloxycarbonyl.

U.S. Pat. No. 3,896,110 discloses a process for preparation of 6-aminopenicillanic acid by reacting a natural penicillin such as Penicillin G or Penicillin V with a phosphorus halide to protect the carboxyl group, reacting this with an acid halide to form the corresponding penicillin imino halide, reacting the imino halide with an alcohol to form an imino ether and subsequent hydrolysis.

SUMMARY OF THE INVENTION

The present invention provides a novel process for preparation of 1,1-dioxopenicillanoyloxymethyl 6-beta-aminopenicillanate of the formula

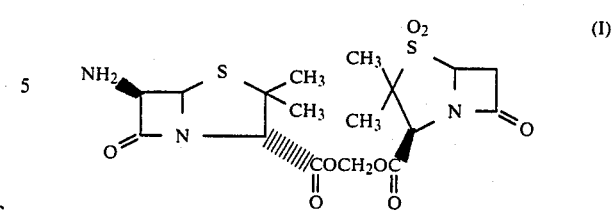

which comprises the steps of (a) contacting a compound of the formula

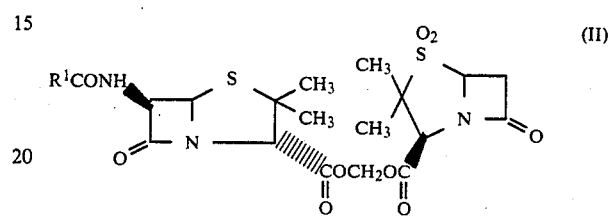

wherein $R^1$ is $C_6H_5CH_2$ or $C_6H_5OCH_2$, under anhydrous conditions with a halogenating agent in the presence of a reaction inert organic solvent and an equimolar amount of a tertiary amine at a temperature of from $-70°$ to $20°$ C. to form an imino halide of formula (III), below, wherein for example, Z is Cl;

(b) contacting said imino halide with a primary alcohol of the formula $R^2OH$ where $R^2$ is alkyl having from one to four carbon atoms at a temperature of from $-70°$ to $0°$ C. to form an imino ether of formula (III), $Z=OR^2$;

(c) contacting said imino ether with water at a temperature of $-70°$ to $0°$ C. to provide the desired product (I).

The invention process has advantages over the prior art methods for providing the coupled amine of formula (I) since the natural penicillin, Penicillin G or Penicillin V, need not be deacylated and the amino group protected prior to coupling with a suitable derivative of penicillanic acid 1,1-dioxide. In the instant process the natural penicillin need only be converted to a salt, e.g. a sodium salt, and this coupled with e.g., chloromethyl 1,1-dioxopenicillanate to provide the starting compound (II) which is then deacylated by the invention process. By the term "halogenating agent" as used herein is meant a reagent which readily converts the starting amide of formula (II) to the corresponding imino halide under the instant process conditions without substantial degradation of the starting material or product. Examples of such halogenating agents are phosphorus pentachloride, phosgene, phosphorus oxychloride, phosphorus oxybromide and oxalyl chloride. A particularly preferred halogenating agent is phosphorus pentachloride.

Particularly preferred tertiary amines for the invention process are pyridine and N,N-dimethylaniline.

The invention further provides valuable intermediates of the formula

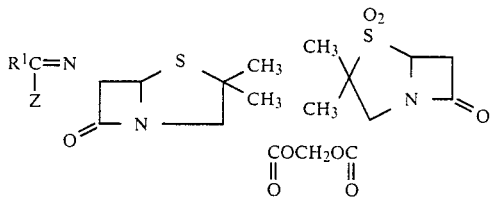

wherein R$^1$ is as previously defined and Z is Cl or OR$^2$ where R$^2$ is as previously defined.

A particularly preferred value for R$^2$ is methyl.

DETAILED DESCRIPTION OF THE INVENTION

This invention relates to derivatives of penicillanic acid which is represented by the following structural formula:

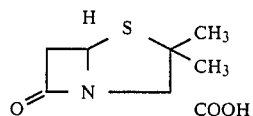

In derivatives of penicillanic acid, broken line attachment ('''') of a substituent to the bicyclic nucleus indicates that the substituent is below the plane of the nucleus. Such a substituent is said to be in the alpha-configuration. Conversely, broad line attachment ( ) of a substituent to the bicyclic nucleus indicates that the substituent is above the plane of the nucleus. This latter configuration is referred to as the beta-configuration. As used herein a solid line attachment ( ) of a substituent to the bicyclic nucleus indicates that the substituent can be either in the alpha-configuration or the beta-configuration.

The reaction of a starting compound of formula (II) as defined above with halogenating agent is carried out in the presence of a reaction inert solvent and a tertiary amine. Illustrative of suitable such solvents are chloroform, dichloromethane, 1,2-dichloroethane and tetrahydrofuran. Especially preferred solvents are chloroform and dichloromethane.

While a wide variety of aliphatic, aromatic and aralkyltertiary amines, for example, pyridine, triethylamine, ethyl diisopropylamine, N,N-dimethylaniline, N,N-diethylaniline, pyridine, picoline, N-methylmorpholine, etc., will afford satisfactory results, particularly preferred tertiary amines are pyridine and N,N-dimethylaniline.

A preferred range of temperature for the first step of the invention process is from about −70° to 20° C. and particularly from about −40° to −20° C.

The compound of formula (II), dissolved in the reaction inert solvent, is cooled to a temperature within the preferred temperature range. To this is added the tertiary amine and halogenating agent. While these reagents may be employed in a wide range of mole ratios relative to the starting compound of formula (II), a preferred molar ratio is from equimolar amounts to a ratio of 1:5:10 [(II):halogenating agent:tertiary amine] and especially preferred is a molar ratio of 1:1–2:2.

The resulting imino halide intermediate is ordinarily not isolated but for reasons of efficiency the solution containing it is used directly in the next step to form the corresponding imino ether of formula (III) wherein Z is OR$^2$ and R$^2$ is as defined above. The conversion of the imino halide to imino ether is carried out by addition of at least an equimolar amount of a primary alcohol, R$^2$OH at a temperature of from −70° to 0° C. The imino ether forms in a short time under these conditions, e.g. within from about 10 minutes to 6 hours. The resulting solution of imino ether intermediate is then contacted with water while stirring the reaction mixture for an additional hour or less at a temperature of from −70° to 0° C.

The resulting 1,1-dioxopenicillanoyloxymethyl 6-beta-aminopenicillanate is then isolated by standard methods known to those of skill in the art. For example, the reaction mixture is concentrated, the residue washed with sodium bicarbonate solution to neutralize residual acids and extracted with a water immiscible solvent from which the desired 6-amino compound of formula (I) is obtained by evaporation of the dried extract.

Alternatively, the reaction mixture containing the 6-amino compound (I) can be acylated prior to isolation and purification of product. For example, the reaction mixture after the hydrolysis step can be acylated with D(-)-2-phenylglycyl chloride hydrochloride or D(-)-2-(4-hydroxyphenyl)glycyl chloride hydrochloride by methods known in the art to form the corresponding 6-acyl compounds of formula (V) which are useful antibacterial agents.

The following Examples and Preparations are provided solely for further illustration. Nuclear magnetic resonance spectra (NMR) were measured for solutions in deuterated chloroform (CDCl$_3$) or deuterated dimethyl sulfoxide (DMSO-d$_6$), and peak positions are reported in parts per million downfield from tetramethylsilane. The following abbreviations for peak shapes are used: bs, broad singlet; s, singlet; d, doublet; t, triplet; q, quartet; m, multiplet.

EXAMPLE 1

1,1-Dioxopenicillanoyloxymethyl 6-(2-phenylacetamido)penicillanate

To a flame dried, magnetically stirred flask, under nitrogen, is added 0.7 g (2.48 mmole) chloromethyl penicillanate 1,1-dioxide and 2 ml dimethylsulfoxide. After stirring to dissolve the mixture, 972 mg (2.73 mmole) sodium 6-phenylacetamidopenicillanate dissolved in 2.5 ml dimethylsulfoxide is added followed by 41 mg (0.25 mmole) potassium iodide. The resulting mixture is stirred overnight at room temperature, 30 ml cold ethyl acetate added and the mixture washed with cold brine (3×30 ml) and cold water (1×30 ml). The combined aqueous layers are backwashed with cold ethyl acetate (30 ml), and the combined organic layers dried (Na$_2$SO$_4$). Evaporation of solvent in vacuo gives 1.29 g of product as a hard tan foam. A one gram sample of the foam is purified by column chromatography on 10 g of silica gel, eluting with ethyl acetate/hexane, 1:1. The product containing fractions were combined and evaporated in vacuo to afford 370 mg of the title compound. $^1$H-NMR (CDCl$_3$) ppm (delta): 1.4–1.48 (m), 1.62 (s), 3.45 (d), 3.65 (s), 4.45 (s), 4.65 (t), 5.3–5.8 (m), 5.9 (s), 6.3 (d) and 7.4 (s). Infrared spectrum (KBr): 1783 cm$^{-1}$.

EXAMPLE 2

1,1-Dioxopenicillanoyloxymethyl 6-(2-phenylacetamido)penicillanate

A. Chloromethyl 6-(2-phenylacetamido)penicillanate

To 10 g (0.028 mole) sodium 6-(2-phenylacetamido)-penicillanate is added 100 ml water, 200 ml methylene chloride and 10.092 g (0.0309 mole) 85% tetrabutylammonium chloride, the mixture is stirred at room temperature for one-half hour and poured into a separatory funnel. The layers are separated, the aqueous layer is extracted twice with methylene chloride and the combined organic layers dried ($Na_2SO_4$) and concentrated in vacuo to afford 16.6 g of soft tan solid. To this is added 50 ml chloroiodomethane and the mixture is stirred under a nitrogen atmosphere overnight. The resulting hazy solution is concentrated in vacuo to a residual oil. The oil is dissolved in 150 ml ethyl acetate, washed in turn with water (5×80 ml), normal sulfuric acid (3×50 ml), 5% sodium bicarbonate solution (3×50 ml), brine (2×80 ml) and dried ($Na_2SO_4$). Evaporation of solvent in vacuo gave a residual hard foam, 11 g. The residue is taken up in 7 ml ethyl acetate, 3 ml hexane is added and the solution placed on a silica gel column and eluted with 1:1 ethyl acetate/hexane. Fifteen fractions of 50 ml each are collected. Fractions 8-12 are combined and concentrated in vacuo to a yellow oil which under high vacuum affords an off-white foam, 5.3 g (49.5%); $^1$H-NMR ($CDCl_3$) ppm (delta): 1.50 (s, 6H), 3.60 (s, 2H), 4.42 (s, 1H), 5.50 to 5.92 (m, 4H), 6.45 (bs, 1H), 7.35 (s, 5H).

B. Under a nitrogen atmosphere, to 383 mg (1 mmole) chloromethyl 6-(2-phenylacetamido)penicillanate in 4 ml acetone is added 33 mg (0.2 mmole) potassium iodide. To this mixture is added a solution of 475 mg (1 mmole) tetrabutylammonium penicillanate 1,1-dioxide in 4 ml acetone. The reaction mixture changes from a yellow solution to a hazy pink color and gradually reverts to a yellow solution. After stirring for about one hour, the reaction mixture is concentrated to dryness in vacuo, to afford 0.82 g of foam. This is taken up in ethyl acetate, 2 g silica gel is added and the mixture evaporated to dryness in vacuo. The residual solid is placed on a column of silica gel (8 g), eluted with 1:1 ethyl acetate/hexane and fractions 7-12 combined. Evaporation of solvent in vacuo gave 260 mg (45%) of the title compound. The infrared spectrum (KBr) was identical to the product of Example 1.

EXAMPLE 3

1,1-Dioxopenicillanoyloxymethyl 6-(2-phenoxyacetamido)penicillanate

A mixture of 1.4 g of potassium 6-(2-phenoxyacetamido)penicillanate, 845 mg of chloromethyl penicillanate 1,1-dioxide, 20 ml of dimethyl sulfoxide and a few milligrams of sodium iodide was stirred at ca. 25° C. overnight. The mixture was poured into 140 ml of ice-water and the pH was adjusted to 8.5. The resultant aqueous system was extracted with ethyl acetate, and the extracts were combined, washed with water, dried ($Na_2SO_4$) and evaporated in vacuo. This afforded 660 mg of crude material.

The crude material was chromatographed on silica gel, using a 1:1 mixture of ethyl acetate and hexane as eluant, and this afforded 230 mg of the title product (13% yield). The IR spectrum (KBr disc) showed an absorption at 1786 $cm^{-1}$. The NMR spectrum ($CDCl_3$) showed absorptions at 7.4 (s), 5.85 (s), 5.45 (s), 5.05 (s), 4.6 (t), 4.43 (s), 4.4 (s), 3.45 (d), 1.62 (s), 1.48 (s), 1.44 (s) and 1.4 (s) ppm.

EXAMPLE 4

1,1-Dioxopenicillanoyloxymethyl 6-beta-aminopenicillanate

To a flame dried flask is added 1.859 g (3.27 mmole) 1,1-dioxopenicillanoyloxymethyl 6-(2-phenylacetamido)penicillanate and 10 ml methylene chloride. The resulting solution is cooled to −30° C., 0.529 ml (6.54 mmole) pyridine and 1.362 g (6.54 mmole) phosphorus pentachloride is added and the mixture stirred at −30° C. for one hour, then stirred in an ice bath for 40 minutes. The resulting clear yellow solution is cooled to −30° C., methanol (16 ml) is slowly added and the resulting mixture is stirred at this temperature for 30 minutes to provide a solution of imino ether (III), $Z=OCH_3$. Water, 9 ml, is then added to the solution of imino ether and the resulting mixture is concentrated in vacuo. The concentrate is poured into cold 5% aqueous sodium bicarbonate solution and extracted with methylene chloride. The combined organic layers are washed with cold brine (5×25 ml), dried ($MgSO_4$) and the solvent evaporated to yield a thin oil. The oil is slowly added to cold ethyl ether (75 ml) and stirred in the cold, under nitrogen for 20 minutes. The resulting colorless precipitate is collected by filtration and dried under high vacuum to yield 552 mg of the title amine. $^1$H-NMR ($CDCl_3$) ppm (delta): 1.33 (s, 3H), 1.49 (s, 3H), 1.45 (s, 3H), 1.58 (s, 3H), 3.4–3.7 (m, 2H), 4.33 (s, 1H), 4.57 (m, 2H), 5.16 (q, 1H), 5.40 (d, 1H), 5.86 (s, 2H).

When the above procedure is repeated starting with 1,1-dioxopenicillanoyloxymethyl 6-(2-phenoxyacetamido)penicillanate, provided in Example 3, in place of the corresponding 6-(2-phenylacetamido)-penicillanate derivative, the results are substantially the same. Likewise, use of any of the following anhydrous alcohols in place of methanol in the above procedures gives the title compound in similar manner: ethanol, n-propanol, isopropanol, isobutanol, n-butanol.

Use of chloroform, acetone, methylene chloride or mixtures thereof as solvent in the above procedures affords the title compound in like manner.

EXAMPLE 5

1,1-Dioxopenicillanoyloxymethyl 6-[D-(2-amino-2-phenylacetamido)]-penicillanate hydrochloride A. To a flame dried flask is added 1.895 g (3.27 mmole) 1,1-dioxopenicillanoyloxymethyl 6-(2-phenylacetamido)penicillanate and 10 ml methylene chloride. The mixture is stirred under nitrogen, cooled to −35° C. (dry ice/acetone), 0.9 ml (7.03 mmole) N,N-dimethylaniline and 0.75 g (3.6 mmole) phosphorus pentachloride is added and the mixture stirred at −35° to −30° C. until all material is dissolved (about 35 minutes). To the resulting clear yellow solution is added 1.14 ml (28.1 mmole) methanol, the mixture is stirred at −22° to −20° C. for 15 minutes to provide the imino ether (III), $Z=OCH_3$. To this 0.2 ml water is added and stirring is continued at the same temperature for an additional 15 minutes.

B. The resulting mixture, containing 1,1-dioxopenicillanoyloxymethyl 6-beta-aminopenicillanate is cooled to −35° C. and 1.83 g (14.3 mmole) N,N-dimethylaniline followed by 0.75 g (3.46 mmole) D(-)-2-phenylglycyl chloride hydrochloride. The resulting thick slurry is stirred for 30 minutes at −20° C., then poured into a 20° C. of 0.240 g sodium bicarbonate in 10 ml water. After stirring for ten minutes, the mixture is poured into a separatory funnel, the layers separated and the aqueous layer extracted with 3×20 ml methylene chloride. The organic layers are combined, washed with brine and dried over anhydrous sodium sulfate. The solvent is evaporated to afford a yellow gummy oil. The oil is taken up in methylene chloride (50 ml) and hexane (ca. 100 ml) slowly added to precipitate a tacky solid. The solvent is decanted and the solid dried in vacuo to give 1.37 g (66%) of foamed solid. The solid is triturated with ethyl ether (2×30 ml), the solvent decanted and the resulting solid taken up in 25 ml methylene chloride. The solution is cooled in a dry ice/acetone bath and hexane (30 ml) slowly added. The mixture is stirred for ten minutes, filtered under nitrogen and the solid product dried in vacuo to afford 1.19 g (57%) of the title compound as a light yellow solid, M.P. 164°–170° C. (decomp.).

The NMR spectrum of the product (in DMSO-$d_6$) showed absorptions at 9.4 (d, 1H), 9.0 (broad s, 2H), 7.4 (m, 5H), 5.8 (s, 2H), 5.4 (m, 2H), 5.1 (broad s, 2H), 4.5 (s, 1H), 4.4 (s, 1H), 3.6 (m, 1H), 3.3 (m, 1H), 1.4 (s, 3H) and 1.3 (s, 6H) ppm downfield from tetramethylsilane. The IR spectrum of the product (KBr disc) showed absorptions at 3400, 2950, 1790, 1690, 1320 and 990 cm$^{-1}$. The $^{13}$C proton decoupled NMR spectrum of the product (in DMSO-$d_6$) showed absorptions at 172.406, 171.931, 167.563, 166.131, 165.749, 133.622, 129.649, 129.015, 128.546, 127.873, 81.0634, 69.7087, 67.1798, 63.9624, 62.2723, 60.6689, 58.6824, 54.8879, 37.6945, 30.1372, 26.4151, 19.6717, 17.7702 downfield from tetramethylsilane.

C. By employing 1,1-dioxopenicillanoyloxymethyl 6-(2-phenoxyacetamido)penicillanate as starting material in the procedure of Part A, above, likewise provides 1,1-dioxopenicillanoyloxymethyl 6-beta-aminopenicillanate. Acylation of this by the procedure of Part B, above, likewise provides the title compound.

EXAMPLE 6

1,1-Dioxopenicillanoyloxymethyl 6-[D-(2-amino-2-phenylacetamido)]penicillanate hydrochloride To 0.055 ml of ethyl chloroformate and 1 drop of N-methylmorpholine in 5 ml of acetone at −15° C., was added, all in one portion, 164 mg of potassium N-(1-methyl-2-methoxycarbonylvinyl)-D-2-amino-2-phenylacetate. Stirring was continued for 30 minutes at −20° C. to −5° C., and then the mixture recooled to −20° C. To this reaction mixture was then added a solution of 353 mg (0.76 mmole) 1,1-dioxopenicillanoyloxymethyl 6-aminopenicillanate in 10 ml chlorform. The resulting mixture was stirred at −20° for 15 minutes and then it was allowed to warm to room temperature. Excess chloroform and water were added and the layers were separated. The organic layer was washed with water at pH 8.5 and then with saturated sodium chloride solution, and then it was dried (Na$_2$SO$_4$) and evaporated in vacuo. The residue was dissolved in a mixture of 3 ml of tetrahydrofuran and 2 ml of water and the pH was adjusted to 1.5 at 0° C. The mixture was stored at 0° C. for 30 minutes and then an excess of 1:1 ethyl acetate-diethyl ether and 5 ml of water were added. The layers were separated and the aqueous layer was washed twice with diethyl ether. The aqueous solution was then lyophilized to give 100 mg of the title compound.

The NMR spectrum of the product (DMSO-$d_6$/D$_2$O) showed absorptions at 7.48 (m, 5H), 5.9 (m, 2H), 5.47 (m, 2H), 5.05 (m, 2H), 4.2 (m, 2H), 3.45 (m, 2H), 1.45 (m, 6H) and 1.36 (m, 6H) ppm downfield from internal tetramethylsilane. The IR spectrum (KBr disc) showed absorptions at 1800–1735 and 1685 cm$^{-1}$.

EXAMPLE 7

1,1-Dioxopenicillanoyloxymethyl 6-[D-(2-amino-2-p-hydroxyphenylacetamido)]-penicillanate hydrochloride To a solution of 341 mg (0.629 mmole) tetrabutylammonium D-[2-(1-methyl-2-methoxycarbonylvinylamino)-2-p-hydroxyphenyl]acetate in 5.0 ml acetone under a nitrogen atmosphere is added one drop N-methylmorpholine, the mixture cooled to −20° C. and after five minutes stirring at this temperature, 0.060 ml (0.628 mmole) ethyl chloroformate is added. Stirring is continued for ten minutes and a methylene chloride solution of 276 mg (0.598 mmole) 1,1-dioxopenicillanoyloxymethyl 6-beta-aminopenicillanate (obtained in Example 4) is added at −30° C. The mixture is stirred while allowing to warm to room temperature. The solvents are evaporated in vacuo, the residue taken up in a mixture of ethyl acetate and water (pH 6.8). The aqueous phase is extracted with ethyl acetate and the combined organic layers washed with brine and dried (Na$_2$SO$_4$). Evaporation of solvent in vacuo gives 375 mg (96%) of crude product. The crude is taken up in acetone (10 ml), water (4 ml) added and mixture adjusted to pH 1.6. The acetone is evaporated, the residue washed twice with ethyl ether and the aqueous layer freeze dried to afford 250 mg (64%) of purified product. $^1$H-NMR (DMSO-$d_6$) ppm (delta): 1.38–1.50 (m, 12H), 3.47 (m, 2H), 4.33 (s, 1H), 4.5 (s, 1H), 4.97 (s, 1H), 5.07 (m, 1H), 5.5 (m, 2H), 5.92 (m, 2H), 7.08 (m, 4H). Infrared (KBr): beta-lactam peak at 1780 cm$^{-1}$.

PREPARATION A

Chloromethyl Penicillanate 1,1-Dioxide

A mixture of 4.66 g of penicillanic acid 1,1-dioxide, 50 ml of dichloromethane and 35 ml of water was treated with sufficient tetrabutylammonium hydroxide (40% in water) to give a pH of 6.0. The dichloromethane layer was separated and the aqueous phase extracted with fresh dichloromethane (2×50 ml). The organic layers were combined, dried over sodium sulfate and concentrated to give 10.1 g of the tetrabutylammonium salt of penicillanic acid 1,1-dioxide.

The above tetrabutylammonium penicillanate 1,1-dioxide was added to 50 ml of chloroiodomethane and the reaction mixture allowed to stir at ambient temperature overnight. The reaction mixture was concentrated to half volume in vacuo, and chromatographed on 200 g of silica gel using ethyl acetate/hexane as the eluant, 12 ml cuts being taken every 30 seconds. Fractions 41–73 were combined and concentrated to dryness to give 3.2 g of the title compound.

The NMR spectrum (CDCl$_3$) showed absorptions at 1.5 (s, 3H), 1.66 (s, 3H), 3.42 (d, 2H), 4.38 (s, 1H), 4.6 (t, 1H) and 5.7 (dd, 2H) ppm.

PREPARATION B

Tetrabutylammonium D-[2-(1-methyl-2-methoxycarbonylvinylamino)-2-(4-hydroxyphenyl)acetate To 300 ml dichloromethane is added 30 g 4-hydroxyphenylglycine and 50 ml water. To this is added 40% aqueous tetrabutylammonium hydroxide to adjust the mixture to pH 8.5. The mixture is allowed to separate, the upper layer is removed, saturated with sodium sulfate, extracted with dichloromethane and the combined organic layers are dried ($Na_2SO_4$) and evaporated in vacuo. The residual tetrabutylammonium 4-hydroxyphenylglycine is added to 150 ml methyl acetoacetate and the mixture is heated at about 65° C. for 10 minutes. The title compound is obtained upon cooling. It is collected by filtration, washed with ethyl ether and air dried.

I claim:

1. A process for preparation of a compound of the formula

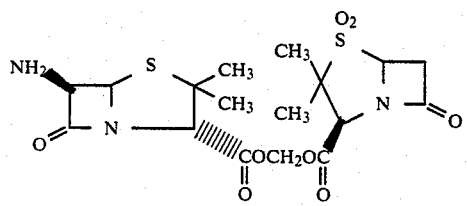

which comprises the steps of (a) contacting a compound of formula

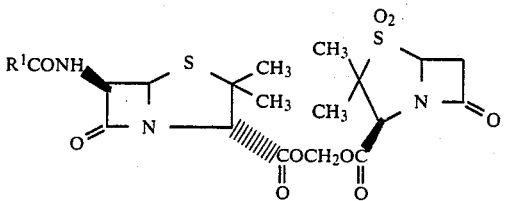

wherein $R^1$ is $C_6H_5CH_2$ or $C_6H_5OCH_2$, under anhydrous conditions with a halogenating agent in the presence of a reaction inert organic solvent and a tertiary amine at a temperature of from −70° to 20° C. to form an imino halide;

(b) contacting said imino halide with a primary alcohol of the formula $R^2OH$ where $R^2$ is alkyl having from one to four carbon atoms, at a temperature of from −70° to 0° C. to form an imino ether;

(c) contacting said imino ether with water at a temperature of from −70° to 0° C.

2. A process according to claim 1 wherein $R^1$ is $C_6H_5CH_2$, said halogenating agent is phosphorus pentachloride and said tertiary amine is pyridine or N,N-dimethylaniline.

3. A process according to claim 1 wherein in steps (a)-(c) said temperature is from about −40° to −20° C.

4. A process according to claim 1 wherein said solvent is dichloromethane.

5. A process according to claim 1 wherein $R^2$ is methyl, ethyl or n-butyl.

6. A compound of the formula

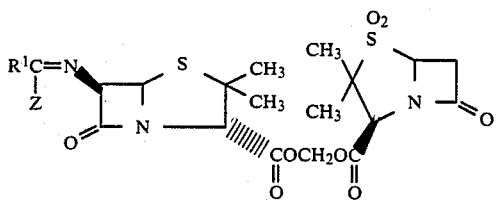

wherein $R^1$ is $C_6H_5CH_2$ or $C_6H_5OCH_2$ and Z is Cl or $OR^2$ where $R^2$ is alkyl having from one to four carbon atoms.

7. A compound according to claim 6 wherein Z is Cl.

8. The compound according to claim 7 wherein $R^1$ is $C_6H_5CH_2$.

9. A compound according to claim 6 wherein Z is $OR^2$ and $R^2$ is methyl, ethyl or n-butyl.

10. A compound according to claim 9 wherein $R^1$ is $C_6H_5CH_2$.

* * * * *

UNITED STATES PATENT AND TRADEMARK OFFICE
CERTIFICATE OF CORRECTION

PATENT NO. : 4,530,792

DATED : July 23, 1985

INVENTOR(S) : Paul D. Weeks

It is certified that error appears in the above-identified patent and that said Letters Patent is hereby corrected as shown below:

At column 3, line 5, in formula (III) insert broad line bonds at positions 6 and 3' and insert broken line bond at position 3

At column 3, line 23, insert broken line bond at positions 3 (to COOH) and 5 (to H).

At column 3, line 30, "(  )" should read -- (◀) --.

At column 3, line 34, "(  )" should read -- (——) --.

Signed and Sealed this

Seventeenth Day of December 1985

[SEAL]

Attest:

DONALD J. QUIGG

Attesting Officer

Commissioner of Patents and Trademarks